United States Patent
Tsunekawa et al.

(10) Patent No.: US 8,354,117 B2
(45) Date of Patent: Jan. 15, 2013

(54) PREPARATION FOR ORAL CAVITY

(75) Inventors: Masayoshi Tsunekawa, Shimonoseki (JP); Kazuyoshi Yokota, Shimonoseki (JP)

(73) Assignee: Nippon Shika Yakuhin Co., Ltd., Shimonoseki-shi, Yamaguchi (JP)

( * ) Notice: Subject to any disclaimer, the term of this patent is extended or adjusted under 35 U.S.C. 154(b) by 0 days.

(21) Appl. No.: 13/387,992

(22) PCT Filed: Jul. 30, 2010

(86) PCT No.: PCT/JP2010/062880
§ 371 (c)(1), (2), (4) Date: Jan. 30, 2012

(87) PCT Pub. No.: WO2011/016395
PCT Pub. Date: Feb. 10, 2011

(65) Prior Publication Data
US 2012/0135059 A1  May 31, 2012

(30) Foreign Application Priority Data
Aug. 6, 2009 (JP) ................. 2009-183093

(51) Int. Cl.
*A61K 8/02* (2006.01)
*A61K 9/00* (2006.01)

(52) U.S. Cl. ............ 424/401; 424/400

(58) Field of Classification Search ........... 424/401
See application file for complete search history.

(56) References Cited

U.S. PATENT DOCUMENTS

| | | | |
|---|---|---|---|
| 4,057,621 A | 11/1977 | Pashley et al. | |
| 4,538,990 A | 9/1985 | Pashley | |
| 5,766,328 A | 6/1998 | Nakabayashi et al. | |
| 6,217,644 B1 | 4/2001 | Matsunae et al. | |
| 2009/0305194 A1* | 12/2009 | Rusin et al. | 433/217.1 |
| 2010/0063176 A1 | 3/2010 | Kato et al. | |
| 2010/0216096 A1* | 8/2010 | Suzuki et al. | 433/217.1 |

FOREIGN PATENT DOCUMENTS

| | | |
|---|---|---|
| JP | 8-225424 A | 9/1996 |
| JP | 10-511956 A | 11/1998 |
| JP | 11-180815 A | 7/1999 |
| JP | 2000-86421 A | 3/2000 |
| JP | 3502390 B2 | 3/2004 |
| JP | 2005-112841 A | 4/2005 |
| JP | 3691442 B2 | 9/2005 |
| JP | 3786288 B2 | 3/2006 |
| JP | 2007-238633 A | 9/2007 |
| JP | 2008-520568 A | 6/2008 |
| JP | 2010-64989 A | 3/2010 |
| WO | 96/17581 A1 | 6/1996 |
| WO | 96/20693 A1 | 7/1996 |
| WO | 97/25967 A1 | 7/1997 |
| WO | 20061055329 A2 | 5/2006 |

OTHER PUBLICATIONS

Yoshiyama et al., "Treatment of cervical hypersensitivity in consideration of esthetic quality", Journal of Dentistry, vol. 34, No. 2, Aug. 1991, pp. 223-229.
International Preliminary Report on Patentability of PCT/JP2010/062880, date of issuance Mar. 13, 2012; 7 pages.

* cited by examiner

*Primary Examiner* — Anne Gussow
*Assistant Examiner* — Doan Phan
(74) *Attorney, Agent, or Firm* — Westerman, Hattori, Daniels & Adrian, LLP

(57) ABSTRACT

Object of the present invention is to provide a preparation for oral cavity that is appropriately usable as a prophylactic agent for dental caries, a therapeutic agent for dental caries at early stage, a prophylactic and/or therapeutic agent for dentinal hypersensitivity, a preparation for the lining of a dentin cavity surface, or the like, which has a superior effect of sealing the dentinal tubules, is capable of improving the acid resistance of the teeth and re-calcifying the teeth, ensures a short-time treatment with an easy operation, and has a high safety and good aesthetic properties. The object is achieved by a preparation for oral cavity such as a prophylactic agent for dental caries and/or a therapeutic agent for dental caries at early stage, a prophylactic and/or therapeutic agent for dentinal hypersensitivity, a preparation for the lining of a dentin cavity surface, or the like, consisting of a liquid (A), in which fluoro-alumino-silicate glass microparticles are dispersed, and an aqueous inorganic phosphoric acid solution (B).

7 Claims, No Drawings

PREPARATION FOR ORAL CAVITY

TECHNICAL FIELD

The present invention relates to a preparation for oral cavity which can be used for a dental treatment such as prophylaxis of dental caries, treatment of dental caries at early stage, prophylaxis and/or treatment of dentinal hypersensitivity, which ensures an effective and short-time treatment.

More specifically, it relates to a preparation for oral cavity having activities of (1) imparting acid resistance to teeth, (2) promoting re-calcification of the teeth, and (3) sealing hypersensitive dentins (open dentinal tubules), by forming microparticles precipitates on surface of tooth within a short time according to a simple process of liquid preparation coating.

BACKGROUND ART

Dental crown has a three-layer structure made of enamel, dentin, and pulp from outside to inside.

The enamel is a hard and highly insoluble layer mainly consisting of hydroxy apatite. However, once exposed to an acidic medium generated by glycolysis of food debris or the like by oral microbes, dissolution (de-calcification) of phosphate ions or calcium ions is promoted and white discoloration (white spots) occurs as an early symptom of dental caries, leading to so-called tooth decay.

As a means of preventing dental caries, fluoride application is known. Specifically, when teeth are treated with a fluoride ion source, hydroxy apatite is modified to fluoroapatite to give acid resistance. Further, it is well known that the treatment has a working effect of promoting formation (re-calcification) of hydroxyapatite by inhibiting dissolution (de-calcification) of phosphate ions or calcium ions, and for example, a treatment for preventing dental caries by application of a fluoride preparation containing a fluoride ion source on tooth surfaces is widely performed.

The preparation generally used as a fluoride preparation in the clinical practice of dentistry is an acidulated phosphate fluoride solution (herein below, abbreviated as "APF"). The working mechanism includes de-calcification of dental component by phosphate due to the acid phosphate property of APF, and the reaction between dissolved calcium ions and fluoride ions yields generation of calcium fluoride on tooth surfaces. However, the problems of APF treatment is that, when exposed to saliva, it is highly likely that the effect is not fully exhibited in an oral cavity. For such reasons, it needs to be maintained for four minutes in a state that the APF is applied on a tooth and intaking of food is prohibited for another 30 minutes or more after that. As such, it has a limit that a dentist may find it fairly troublesome to carryout and a burden on a patient is huge. It is also known that, as calcium fluoride precipitated on tooth surfaces is dissolved in saliva under a de-calcification (acidic) environment, the effect of promoting re-calcification is insufficient.

Composition for oral cavity containing a calcium ion source, a phosphate ion source, and calcium phosphate or the like as well as a fluoride ion source is reported. By simultaneously precipitating calcium fluoride and calcium phosphate on tooth surfaces, an effect of preventing dissolution in saliva under a de-calcification (acidic) environment and promoting re-calcification is expected.

In this connection, a preparation containing separate preparations of a fluoride ion source and a calcium ion source, that are admixed with each other at the time of use, is studied. For example, disclosed in patent document 1 is a product for re-calcification of tooth enamel comprising the first component (first liquid) containing water soluble calcium salts and the second component (second liquid) containing water soluble phosphate salt and water soluble fluoride salt, and it is specifically described that " . . . applied . . . after mixing the first solution with the second solution" (Patent Document 1, page 9, lines 7-8). However, according to the patent document, it is intended to repeatedly carry out the cycle plural times, wherein a single cycle consists of treatment for 5 min and re-calcification for 60 min in saliva. Thus, there is no intention of obtaining microparticles precipitates during a short time (e.g., during dental treatment) as described in the present invention.

For the purpose of re-calcification of de-calcified enamel (dental caries at early stage), (1) a composition for generating calcium phosphate and calcium fluoride by mixing water soluble calcium salts of the first liquid with water soluble phosphate salt and water soluble fluoride salt of the second liquid on tooth surfaces (see for example, Patent Documents 1 to 3 and 8), and (2) a composition for generating calcium phosphate (see for example, Patent Document 9) are suggested.

Primary particles of calcium fluoride that are generated by mixing a fluoride ion source and a calcium ion source are disadvantageous in that they form secondary particles with large particle diameter by self-aggregation and may not easily adsorb on tooth surfaces. As such, a preparation added with a calcium fluoride inhibitor to delay the aggregation (see for example, Patent Document 2) or a composition for oral cavity allowing easy adsorption of calcium fluoride in microparticles state on tooth surfaces by mixing liquid A containing a compound for supplying a polyol phosphoric acid ion (specifically, calcium glycerophosphate) and a compound for supplying a monofluorophosphoric acid ion and liquid B containing sodium fluoride at the time of use to control aggregation rate is reported (see for example, Patent Document 3).

However, the former is problematic in that adsorption of fluoride on tooth surfaces is also inhibited by addition of calcium fluoride inhibitor and the latter is problematic in that stability of the solution containing calcium glycerophosphate ion and a compounds for supplying monofluorophosphoric acid ion remains unsatisfactory.

It is believed that glass ionomer cement, which is one type of dental cements, is expected for its activity of strengthening teeth by the fluoride contained as a glass component. Having superior biocompatibility, adhesiveness, and aesthetics, the glass ionomer cement is widely used for filling dentin cavity, a crown, an inlay or adhesion of a bridge or an orthodontic bracket. However, when it is in contact with water such as saliva in early hardening stage, the hardening reaction is inhibited and inferior physical properties are obtained in the end. Further, as there are drawbacks that the polished surface after hardening is coarse and film is thick so that feelings in tongue or aesthetics are poor, efforts are being made to improve them. As a method of improving coarseness of a polished surface or film thickness, use of powder for glass ionomer cement having specific gravity of 2.4 to 4.0, mean particle diameter of 0.02 to 4 μm, and BET specific surface area of 2.5 to 6.0 $m^2/g$ is suggested (see for example, Patent Document 4). However, as a specific example, only the powder with mean particle diameter of 2.0 to 2.2 μm and maximum particle diameter of 3.49 to 3.95 μm is disclosed. As described therein, the dental glass ionomer cement powder is the same as cement used in construction and it is first mixed with a liquid exclusive for cement and then used. Therefore, using itself as a liquid preparation is not supposed and examples therefor are not described either.

In clinical dentistry, it is reported that a severe pain is caused not only by dental caries but also by hypersensitivity. As explained above, a dental crown has a three-layer structure made of enamel, dentin and pulp, and dentinal tubules are extended all over the dentin. Although the dentinal tubules are generally covered by enamel, gum or the like, dentinal hypersensitivity is often caused when the dentinal tubules are opened for some reasons. For example, even when the dentinal tubules are exposed or opened by dental caries, use of a dental preparation containing abrasives, abrasion by bleaching carried out for aesthetic purpose, gum recession caused by aging, or the like, temporal but severe pain is caused by cold water or touch stimulation.

The mechanism of developing dentinal hypersensitivity is not fully elucidated. However, hydrodynamics is considered as a strong candidate. According to the hydrodynamics, various stimulations applied on dentin cause migration of fluid in dentinal tubules to excite the nerve fiber on the pulp side.

Thus, a treatment of inhibiting the migration of fluid in dentinal tubule is effective for improving dentinal hypersensitivity and it is reported that, as exemplified by coating a varnish containing a solvent and a resin for sealing a tooth, dentinal hypersensitivity is ameliorated or removed by sealing the dentinal tubules.

Examples of the methods for treating dentinal hypersensitivity are as follows; (1) treatment method for sealing dentinal tubules: in addition to potassium oxalate, a resin, strontium chloride, silver diamine fluoride, HY preparation, sodium fluoride solution, pasta added with sodium fluoride, a calcium hydroxide preparation, ion introduction or the like (Journal of Dentistry, August 1991, Vol. 34, No. 2), (2) treatment method for coating an exposed dentin: cement, paraform added dressing or the like, (3) restoration of a defective area: glass ionomer cement, adhesive resin or the like, (4) treatment by sedation of pulp nerves: administration of an anti-inflammatory pain-relieving agent, irradiation of soft laser or the like, and (5) pulp extraction.

Among them, adhesive resin or the glass ionomer cement having adhesiveness for teeth of (3) forms a strong film that is very difficult to remove. Thus, it is not appropriate for a case in which periodontal regeneration therapy on root canal surface may be applied.

Only a temporal effect is obtained from (4), and according to (5), the pulp, that is, nerves, is completely removed and blood vessels are removed together with nerves, and as a result, teeth are sacrificed even though the pains are completely eliminated.

The above (1) and (2) are a therapeutic method which does not involve a sacrifice of pulp or teeth, and therefore are appropriate for a case in which no major defect exists. However, care should be taken when choosing (2), because some cement has low pH. According to a dressing added with paraform, paraformaldehyde as a component has an effect of fixing pulp. However, it is difficult to say that it is fully safe to be applied in an oral cavity. Among those described in (1), a sodium fluoride solution and pasta added with sodium fluoride generally use 2% sodium fluoride (neutral). However, as it does not seal dentinal tubules, the effect of inhibiting hypersensitivity is very minor. When used for the purpose of protecting pulp, calcium hydroxide is effective. However, it has a very little effect on general dentinal hypersensitivity such as cold water pain. Ion introduction is a method of impregnating an ion tray in 2% sodium fluoride solution (neutral) and aggressively introducing fluoride with an aid of electric current, which requires an expensive device for introducing fluoride ions.

Further, according to (1) and (2), only a material containing effective components is applied on tooth surfaces, and therefore the effect is often temporary.

When the particle diameter of the material is smaller than diameter of dentinal tubules and the reaction between the two liquids occurs within the dentinal tubules to generate microparticle reaction products (that is, precipitates) within a short period of time, the dentinal tubules can be sealed. Further, when the microparticles evenly cover dentinal surface to seal the dentinal tubules, stimulation on the tubules is blocked, and therefore a huge therapeutic effect can be expected. To accomplish it, studies on physical properties of the material are required. In this regard, it is difficult to say that a sufficient improvement has been made with conventional materials.

The HY preparation (trade name: HYC) is mixture powder of tannin, zinc fluoride, strontium fluoride and zinc oxide. Although inhibition of hypersensitivity by an astringent effect of tannin and prevention of dental caries by fluoride are expected, as it instantly hardens in contact with water, it has a problem in handlability. There is also a problem that the cured product is colored with a dark color in an oral cavity.

Silver diamine fluoride preparation (trade name: SAFORIDE) can be easily coated on tooth surfaces and remain on the surfaces for a long period of time so that it has a superior effect of treating hypersensitivity and preventing secondary dental caries. However, due to precipitation of silver, coated tooth area is darkened like a black tooth. Thus, having a significant problem in aesthetics, its application is limited.

Regarding (3), a tooth neck not covered with enamel can be easily abraded by brushing and dentinal tubules are easily exposed in an abraded region to cause hypersensitivity. For other cases in which the dentinal tubules are exposed, the corresponding tooth area is filed and filled with cement or an adhesive resin to perform simultaneously the treatment of hypersensitivity and the restoration of a defective area. However, dentinal characteristics of the hypersensitivity include that no caries (soft dentin) are seen and a treatment without filing a healthy teeth is required.

Under the circumstances, presently, the strongest candidate of therapeutics for dentinal hypersensitivity is a method of using oxalate as reported in Patent Documents 6 and 7. 30% Aqueous solution of potassium oxalate provided by Protect, USA is clinically used as a therapeutic agent for dentinal hypersensitivity (Dentin Desensitizer) while a two-liquid set containing 30% aqueous solution of potassium oxalate and 3% aqueous solution of potassium hydrogen oxalate provided by O. P. Laboratories is also clinically used as a therapeutic agent for dentinal hypersensitivity (Dentin Desensitizer) (see for example, Patent Documents 6 and 7). However, none of them exhibits re-calcification or a prophylactic effect against secondary dental caries.

It is preferable that a treatment with a therapeutic agent for dentinal hypersensitivity is done within a short period of time, that is, it is washed with water within several tens of seconds after applied on tooth surfaces during dental treatment. Further, it preferably has not only an effect of inhibiting hypersensitivity but also an effect of preventing and treating secondary caries. Further, if there is no problem in terms of aesthetics, it can be expected to be used as a material which is applicable for a wide range of cases.

Meanwhile, a material allowing penetration of a mixture liquid into dentinal tubules or early caries lesions and production of nanoparticle precipitates within a short period of time, additionally comprising, in the precipitates, calcium phosphate or a fluoride compound based on expectation of obtaining calcification is desired. However, a material fully satisfying such conditions is not reported yet.

A dental composition for dentinal hypersensitivity comprising aqueous polymer emulsion particles, which have a smaller particle diameter than diameter of dentinal tubules so that it can react with a calcium compound and form a larger aggregate than the diameter of dentinal tubules, is suggested (Patent Document 5). However, it does not exhibit re-calcification or an effect of preventing secondary dental caries.

Pain may be caused by temperature stimulation or the like after having a dentin cavity or receiving a dental prosthetics. When dental caries are under progress or the like, a dentin cavity is formed as deep as near pulp, and therefore pain is often seen even after the treatment. To avoid it, a lining cement is placed on a dentin cavity surface close to pulp by using calcium hydroxide, glass ionomer cement, or the like. However, although having a high pulp protection effect, calcium hydroxide has no adhesiveness on teeth and is easily desorbed. Thus, an additional lining with other cements is required over the calcium hydroxide layer, and therefore it is laborious. The glass ionomer cement has problems such as discussed above.

PRIOR ART DOCUMENTS

Patent Documents

[Patent Document 1] Japanese Patent No. 3786288
[Patent Document 2] Japanese Unexamined Patent Application Publication (Translation of PCT Application) No. 10-511956
[Patent Document 3] Japanese Unexamined Patent Application Publication No. 2005-112841
[Patent Document 4] Japanese Unexamined Patent Application Publication No. 11-180815
[Patent Document 5] Japanese Patent No. 3502390
[Patent Document 6] U.S. Pat. No. 4,057,621
[Patent Document 7] U.S. Pat. No. 4,538,990
[Patent Document 8] Japanese Patent No. 3691442
[Patent Document 9] Japanese Unexamined Patent Application Publication No. 2007-238633

Non-Patent Documents

[Non-patent Document 1] Journal of Dentistry, August 1991, Vol. 34, No. 2, pages 223-229.

SUMMARY OF THE INVENTION

Object to be Solved by the Invention

As described above, until now only silver diamine fluoride is known to exhibit both functions of suppressing hypersensitivity and preventing dental caries at a sufficient level. However, because black-pigmented teeth are yielded in an application area due to precipitation of silver, there is a significant problem in aesthetics.

The acidic fluoride treatment for preventing dental caries requires a relatively long holding time for moisture exclusion (about 4 min.), thus it is inconvenient for both a dentist and a patient. Further, according to a composition for oral cavity in which a water soluble calcium ion source and a water soluble phosphate ion source are added in addition to a water soluble fluoride ion source, even when the fluoride ion source and the calcium ion source are individually prepared in different preparations (two liquids) that are mixed at the time of use, calcium phosphate is instantly formed in a mixture when a first liquid and a second liquid are admixed with each other. As a result, there is a problem that calcium phosphate may not be selectively introduced on tooth surfaces and may not easily be adsorbed thereon.

Under the circumstances, object of the present invention is to provide a preparation for oral cavity that is appropriately usable as a prophylactic agent for dental caries, a therapeutic agent for dental caries at early stage, a prophylactic and/or therapeutic agent for dentinal hypersensitivity, a preparation for the lining of a dentin cavity surface, or the like, which has a superior effect of sealing the dentinal tubules, is capable of improving the acid resistance of the teeth and re-calcifying the teeth (preventing dental caries and treating dental caries at early stage), ensures a short-time (10 to 20 seconds) treatment with an easy operation, and has a high safety and good aesthetic properties.

Means to Solve the Object

As a result of conducting intensive studies, inventors of the present invention found that, by dispersing fluoro-alumino-silicate glass, which has been conventionally used as powder, in water in a microparticle state, a stable dispersion is obtained without having any precipitation, and according to a simple operation of mixing the dispersion with a separately prepared water soluble phosphate solution at the time of use and applying on tooth surfaces, microparticle precipitates of silicate cement containing calcium phosphate and calcium fluoride are formed on an area of dental caries or an exposed dentin area. It was also found that, by adjusting pH of the mixture liquid, microparticle precipitation on tooth surfaces is ensured, and as a result, sealing of dentinal tubules can be obtained without re-calcification. The present invention is completed accordingly.

In particular, pH at the time of application on tooth surfaces is critical. In an early stage of an application on tooth surfaces, Ca ions derived from tooth de-calcification are utilized. As such, the working liquid, that is, a liquid that is obtained by mixing the liquid (A), wherein microparticles of fluoro-alumino-silicate glass are dispersed, and the aqueous inorganic phosphoric acid solution (B) at the time of use, is controlled to be in an acidic region (pH 2 to 4) enabling tooth de-calcification in an early stage of mixing while it is slowly shifted to a region of pH 4 to 6 at which calcium phosphate and calcium fluoride precipitate in a final stage of application.

In this regard, the liquid according to the prior art techniques described above is to be applied on tooth surfaces in a weakly acidic to neutral state, and therefore tooth de-calcification as disclosed in the present invention is not suggested at all.

For example, it is described in Patent Document 1 that "Unexpectedly, a result exhibiting that the solution has pH of about 4.5 to 10, and preferably pH of about 5.5 to 7 is obtained. At pH lower than about 3, demineralization occurs rapidly. pH less than 2.5 is generally not desirable from the viewpoint of safety" (Patent Document 1, page 9, lines 12-15). The liquids of Patent Documents 2, 3, 8 and 9 are all neutral at the time of their application, and therefore tooth de-calcification is not intended in those works.

Provided by the present invention is a preparation for oral cavity which is suitable as a prophylactic agent for dental caries and a therapeutic agent for dental caries at early stage, a prophylactic and/or therapeutic agent for dentinal hypersensitivity, a preparation for the lining of a dentin cavity surface, or the like, consisting of a liquid (A), in which fluoro-alumino-silicate glass microparticles are dispersed, and an aqueous inorganic phosphoric acid solution (B).

Microparticles of fluoro-alumino-silicate glass contain, as a constitutional element, Si: 5 to 25% by mass, Al: 5 to 35% by mass, F: 1 to 25% by mass, and at least one selected from Na, K, and Mg: 1 to 10% by mass in total. As an additional constitutional element, it may contain an alkali earth metal such as Ca, Sr and Ba or a metal element such as Zr, La, Y and Ti.

The microparticles of fluoro-alumino-silicate glass have particle diameter at 50% position (D50) of 1 μm or less and particle diameter at 90% position (D90) of 2.5 μm or less when measurement is made from the small diameter side in the volume-based particle size distribution, and those having D50 of 0.5 μm or less and D90 of 2 μm or less are preferred.

It is preferable that the liquid (A), in which microparticles of fluoro-alumino-silicate glass are dispersed, has pH of 6 to 12, the aqueous inorganic phosphoric acid solution (B) has pH of 0.5 to 4, and the mixture liquid of (A) and (B) has pH of 2 to 4 right after their mixing.

According to the present invention, it is believed that the principles for re-calcification are as follows.

The Ca ions eluted by teeth de-calcification caused by phosphoric acid lead to precipitation of calcium phosphate on tooth surfaces. Such Ca ions also react with fluoride ions dissolved from microparticles of fluoro-alumino-silicate glass to cause precipitation of calcium fluoride. Microparticles of fluoro-alumino-silicate glass after dissolution of the fluoride ions react with phosphoric acid to cause precipitation of silicate cement. According to observation using an electron microscope, such precipitates form a mixture layer of microparticles (about 0.01 to 1.0 μm) on tooth surfaces. In this regard, when pH of a liquid applied to tooth surfaces is suitably controlled, the precipitates formed as above are strongly fixed on tooth surfaces. In other words, pH is slowly modified from an early stage to final stage of application so that, in an early stage of tooth surface application, low pH, specifically pH of 2 to 4 for teeth de-calcification, is adopted, and in a final stage of application, pH of near 4 to 6 is adopted to precipitate calcium phosphate and calcium fluoride. With the microparticle precipitates formed therefrom, de-calcified teeth are re-calcified and the microparticle precipitates penetrate into exposed dentinal tubules to seal them, and as a result, hypersensitivity may be treated.

Effect of the Invention

Conventionally, fluoro-alumino-silicate glass has been used in powder form for a dental preparation. However, there are problems that it takes time for treatment including mixing with a liquid preparation at the time of use, and also the particle size is big and tongue feeling and aesthetics are poor. In this connection, a dispersion which is obtained by pulverizing fluoro-alumino-silicate glass to give particle diameter (D90) of 2 μm or less and dispersing the particles in water can be stored in a very stable manner, and liquid/liquid mixture application can be carried out instead of conventional solid (powder)/liquid mixture application. Because the glass powder is dispersed in a microparticle state, a fast reaction is obtained upon application and precipitation is completed within a short time without requiring any holding time.

In other words, precipitates of the microparticles (that is, CaF2, Ca phosphate, and silicate cement as a reaction product) that are formed on tooth surfaces according to a simple operation of mixture liquid application not only protect the dental caries but also promote re-calcification. In addition, as the precipitates can enter dentinal tubules to precipitate a reaction product (that is, CaF2, Ca phosphate, and silicate cement) of the microparticles in the dentinal tubules and seal the exposed dentinal tubules, they can be used as an agent for treating dentinal hypersensitivity having a superior dentinal tubule-sealing effect, an immediate effect, and a superior long-acting property. Further, the precipitates are not easily detached by brushing or the like. Therefore, the present invention enables efficient introduction of a great amount of fluorides on teeth by a short-time treatment. Further, by having precipitates of the microparticles formed on a desired area at micro level such as dentinal tubules or de-calcified dental caries, which are difficult to be treated by conventional cement materials, it can be used as a prophylactic agent for dental caries and a therapeutic agent for dental caries at early stage, a prophylactic and/or therapeutic agent for dentinal hypersensitivity, a preparation for the lining of a dentin cavity surface, or the like.

As a way of preventing dental caries, there are methods as follows: (1) teeth are given with acid resistance so that the tooth-constituting components are difficult to be dissolved in an acid, that is a direct cause of dental caries, and (2) re-calcification of tooth is promoted so that dissolved tooth components are replenished more.

By applying a mixture liquid of the present invention on a tooth, microparticles of calcium fluoride, calcium phosphate, and silicate cement are formed on tooth surfaces, and therefore fluoride ions, phosphate ions, and Ca ions can be provided thereon. As a result, teeth can be treated within a short time (10 to 30 sec) so that a burden to people who receive a dental treatment (in particular, children) can be significantly reduced. In addition, because calcium fluoride and calcium phosphate are simultaneously formed inside a silicate cement layer, calcium fluoride can be introduced to teeth without any dissolution (that is, fluoroapatite is formed) even under de-calcifying (that is, acidic) condition, acid resistance of the teeth is improved, and the re-calcification is promoted. Meanwhile, for hypersensitivity having open dentinal tubules, sealing effect against dentinal tubules can be increased. Since the treatment time according to the present invention is short, that is, from 10 to 30 seconds, and washing with water can be carried out after application, it is not involved with unpleasant acidic taste as in the acidic fluoride treatment and a problem associated with accidental intake, and holding time of four minutes at the time of application or prohibition of food and drink intake for several tens of minutes after the application is not necessary. Thus, an effort of a dentist or a burden to a patient is significantly reduced and feeling of use as a preparation for oral cavity can be improved to a great extent.

Thus, the preparation for oral cavity according to the present invention enables obtainment of an effect of suppressing dentinal hypersensitivity and also a superior effect of preventing dental caries and treating dental caries at early stage.

In the advanced stage of dental caries, soft dentins are removed and a dentin cavity is formed and filled or restored using prosthetics. At that time, by applying the mixture liquid of the present invention on the wall of a dentinal cavity, progress of dental caries can be suppressed more as described above, and the mixture liquid of the present invention is also useful as a lining material for a dentin cavity surface which has a prophylactic activity for dentinal caries and a prophylactic and/or therapeutic effect for dentinal hypersensitivity after filing.

Further, the material of the present invention is very useful as a lining material as it can be applied on dentin surfaces during dental treatment and washed away with water several tens of seconds later, so that the treatment can be completed in a short time. Once the lining formed, an immediate filling treatment can be followed and also impression taking for having dental prosthetics can be performed right after forming lining. Further, the material of the present invention has an effect of prophylactic and therapeutic effect for secondary dental caries as well as an effect of suppressing hypersensitivity. Further, it is a material for oral cavity which can be expected to be used as a material superior in aesthetics and applicable for a broad range of cases. Specifically, not only it exhibits a superior prophylactic and/or therapeutic effect for typical dentinal hypersensitivity and dental caries at early stage, but also it can be applied for abroad range of cases including suppression of hypersensitivity and prophylaxis of secondary dental caries which occur after basic periodontal treatment (field of periodontal disease), suppression of hypersensitivity and prophylaxis of secondary dental caries in an area having an inlay or a crown (field of dental prosthetics), treatment of dental caries on dental root surfaces (field of dental conservation), and treatment of whitened teeth (enamel caries at early stage) occurring near orthodontic brackets without filing (field of dental orthodontics).

MODE OF CARRYING OUT THE INVENTION

According to the present invention, fluoro-alumino-silicate glass contains, as a constitutional element, Si: 5 to 25% by mass, Al: 5 to 35% by mass, F: 1 to 25% by mass, and at least one selected from Na, K, and Mg: 1 to 10% by mass in total. As an additional constitutional element, it may contain an alkali earth metal such as Ca, Sr, and Ba or a metal element such as Zr, La, Y, and Ti.

As a fluoro-alumino-silicate glass, glasses that are used for a chemical-curable type and a photo-curable type glass ionomer cement product used as a filler, a sealant, or an adherent (e.g., FUJI I (manufactured by GC Corporate Center), HY-BOND GLASS IONOMER CX (manufactured by SHOFU INC.), TOKUYAMA IONOTITE F (manufactured by TOKUYAMA DENTAL CORPORATION) or the like), or the glasses with the composition as disclosed in Japanese Unexamined Patent Application Publication Nos. 11-180815 and 2002-60342 can be used. In addition, a glass obtained by mixing an appropriate amount of each compound including silicon oxide, aluminum oxide, calcium phosphate, aluminum phosphate, sodium fluoride, sodium monofluorophosphate and tin fluoride as a source of each constitutional ion and melting and rapidly cooling the mixture can be also used.

According to the present invention, the fluoro-alumino-silicate glass is pulverized to have average particle diameter (D50) of about 2 to 5 µm in a volume-based particle size distribution by using a common pulverizer such as a ball mill and a jet mill, and further micropulverized by using a pulverizer such as a wet micropulverizer•disperser (bead mill) to obtain microparticles with particle diameter of 2 µm or less at 90% position (D90) when measurement is made from the small diameter side in the volume-based particle size distribution. When the particle diameter is greater than 2.5 µm, dispersability is lowered, and as a result not only the aggregates or precipitates are easily formed during storage but also large particles are adhered on applied tooth surfaces at the time of use. Consequently, the dentinal tubule sealing effect, or re-calcification or prophylactic effect against secondary dental caries may not be obtained at a sufficient level.

Stable dispersion of the fluoro-alumino-silicate glass microparticles (herein below, referred to as "liquid A") is obtained by adding powder of fluoro-alumino-silicate glass in an amount of 0.5% by mass to 45% by mass, preferably 1% by mass to 30% by mass, and more preferably 5% by mass to 20% by mass in a medium such as water and pulverizing it with a pulverizer such as a bead mill which is capable of performing micropulverization. When the fluoro-alumino-silicate glass microparticles are less than 0.5% by mass, concentration of the fluoro-alumino-silicate glass microparticles becomes too low so that only insufficient amount of precipitates such as calcium fluoride is obtained when they are admixed/applied with an aqueous inorganic phosphate solution (herein below, referred to as "liquid B"). On the other hand, when it is more than 45% by mass, viscosity of the liquid A is too high so that it may not be easily used.

As a medium, water is preferable. However, from the viewpoint of enhancing stability of the liquid A, a water soluble solvent such as propylene glycol and polyethylene glycol, which is not affected by washing with water at the time of application on tooth surfaces, may be added.

The liquid A is prepared to have pH of 6 to 12, and preferably 6.5 to 10.5, depending on constitutional elements of the glass. However, it can be also adjusted by adding a pH adjusting agent such as hydrogen phosphate salt and hydrogen sulfate salt at the time of preparing dispersion. If so desired, to a dispersion of the fluoro-alumino-silicate glass microparticles, a dispersing agent such as hexametaphosphoric acid salt and polyphosphoric acid salt and a fluoride ion-supplying substance such as sodium fluoride or stannous fluoride can be added within a range that the dispersion stability is not impaired.

According to the present invention, the liquid B is prepared by dilution of conc. phosphoric acid. However, it can be also added with one or more species of inorganic phosphoric acid such as potassium hydrogen phosphate, potassium dihydrogen phosphate, calcium phosphate, monopotassium phosphate, sodium metaphosphoric acid, monosodium phosphate, potassium orthophosphate, sodium orthophosphate, ammonium orthophosphate, and calcium orthophosphate, and it is an aqueous solution containing 0.5% by mass to 50% by mass, preferably 1 to 30% by mass, and more preferably 5% by mass to 20% by mass of phosphate ions in total.

According to the present invention, the mixture liquid obtained by mixing the liquid A having pH of 6 to 12 and the phosphoric acidic liquid B having pH of 0.5 to 4 preferably has pH of 2 to 4 right after the mixing. Within this specific range, calcium ions contained in teeth can be efficiently dissolved in short time as calcium phosphate, calcium fluoride or silicate cement and fixed on tooth surfaces. As a result, the addition amount of fluoride to the teeth is increased, and the fluorides are adsorbed on the teeth as calcium fluoride. When pH of the mixture liquid is lower than 2, there is a risk of having excessive de-calcification and fluoride intake amount is reduced as calcium fluoride is dissolved. On the other hand, when pH is greater than 4, the reaction between phosphate, glass, and teeth is slowed down. As a result, a long period of time is required to obtain precipitates, and therefore undesirable.

According to the present invention, an appropriate amount of the liquid A and liquid B is taken and mixed with each other at the time of use, and directly applied on the area to be treated (area with dental caries or dentinal hypersensitive area) or tooth surfaces having a dentin cavity, and maintained for 10 to 30 seconds to form a film consisting of precipitates of silicate glass microparticles containing calcium fluoride and calcium phosphate. Further, the liquid A and liquid B may be individually applied on tooth surfaces and then mixed with each other thereon.

As a commercial preparation, the liquid A and liquid B of the present invention may be prepared in separate packages, or in a package such as a kit in which the liquid A and liquid B are combined.

EXAMPLES

Herein below, the present invention is explained in greater detail in view of the Examples and Comparative examples. However, it is evident that the present invention is not limited by these examples. In the following Examples, the term "%" represents "% by mass".

Example 1

(1) Production of Dispersion of Fluoro-Alumino-Silicate Glass Microparticles (Liquid $A_1$)

$SiO_2$: 25.8 g, $Al_2O_3$: 20.9 g, $CaF_2$: 17.8 g, $La_2O_3$: 16.4 g, $Ca_2(H_2PO_4)_2$: 9.43 g, $Na_2CO_3$: 15.9 g, and CaO: 0.50 g were fully mixed and stirred in a mortar. The obtained batch was placed in a porcelain crucible and heated in an electric furnace to 1100° C. with a temperature increase rate of about 7° C./min. After keeping it for 5 hours, the molten liquid was poured in water and rapidly cooled to obtain glass. The glass obtained was pulverized with a ball mill (wet type) to obtain fluoro-alumino-silicate glass powder ($a_1$) having average particle diameter (D50) of 3.2 μm in volume-based particle size distribution. The fluoro-alumino-silicate glass powder ($a_1$) was treated for 90 min with a wet type micropulverizer/disperser (bead mill: NANO GETTER DMR110, manufactured by Ashizawa Finetech Ltd.) with rim speed of 10 m/s (beads used: $ZrO_2$ 0.2 mm) while purified water is used as a medium at 15% concentration. As a result, dispersion of the fluoro-alumino-silicate glass microparticles (liquid $A_1$), which has average particle diameter (D50) of 0.38 μm in volume-based particle size distribution and particle diameter of 0.77 μm at 90% position (D90) measured from the small diameter side in the volume-based particle size distribution, was obtained. The glass dispersion (liquid $A_1$) has pH of 8.6.

(2) Production of Aqueous Inorganic Phosphoric Acid Solution (Liquid $B_1$)

Conc. phosphoric acid was diluted with purified water to obtain 10% aqueous solution of inorganic phosphoric acid (liquid $B_1$) (pH: 0.81).

Example 2

(1) Production of Dispersion of Fluoro-Alumino-Silicate Glass Microparticles (Liquid $A_2$)

$CaF_2$: 51.5 g, CaO: 16.3 g, $SiO_2$: 12.1 g, $Al_2(HPO_4)_3$: 8.26 g, $Al_2O_3$: 7.23 g, and $Na_2AlF_6$: 4.52 g were fully mixed and stirred in a mortar. The obtained batch was placed in a porcelain crucible and heated in an electric furnace to 1100° C. with a temperature increase rate of about 5° C./min. After keeping it for 5 hours, the molten liquid was poured in water and rapidly cooled to obtain glass. The glass obtained was pulverized with a dry type jet mill to obtain fluoro-alumino-silicate glass powder ($a_2$) having average particle diameter (D50) of 2.4 μm in volume-based particle size distribution. The fluoro-alumino-silicate glass powder ($a_2$) was treated for 90 min in the same manner as Example 1 using a bead mill with rim speed of 10 to 15 m/s (beads used: $ZrO_2$ 0.3 mm) at 13% concentration. As a result, dispersion of the fluoro-alumino-silicate glass microparticles (liquid $A_2$), which has average particle diameter (D50) of 0.42 μm in volume-based particle size distribution and particle diameter of 1.27 μm at 90% position (D90) measured from the small diameter side in the volume-based particle size distribution, was obtained. The glass dispersion (liquid $A_2$) has pH of 10.2

(2) Preparation of Aqueous Inorganic Phosphoric Acid Solution (Liquid $B_2$)

Conc. phosphoric acid was diluted with purified water to obtain 15% aqueous solution of inorganic phosphoric acid (liquid $B_2$) (pH: 0.67).

Example 3

(1) Production of Dispersion of Fluoro-Alumino-Silicate Glass Microparticles (Liquid $A_3$)

By using $SiO_2$: 40.3 g, $Al_2O_3$: 33.8 g, $Na_2CO_3$: 15.5 g, $Al_2(HPO_4)_3$: 7.77 g, $Na_2AlF_6$: 5.31 g, $ZrO_2$: 2.82 g, $La_2O_3$: 0.24 g, and $Y_2O_3$: 0.79 g, glass was prepared by the same procedure as Example 1 and fluoro-alumino-silicate glass powder ($a_3$) having average particle diameter (D50) of 4.8 μm in volume-based particle size distribution was obtained. With the fluoro-alumino-silicate glass powder ($a_3$) having 10% concentration treated in the same manner as Example 1 using a bead mill, dispersion of the fluoro-alumino-silicate glass microparticles (liquid $A_3$) which has average particle diameter (D50) of 0.33 μm in volume-based particle size distribution and particle diameter of 1.44 μm at 90% position (D90) measured from the small diameter side in the volume-based particle size distribution was obtained. The glass dispersion (liquid $A_3$) has pH of 7.3.

(2) Preparation of Aqueous Inorganic Phosphoric Acid Solution (Liquid $B_3$)

Conc. phosphoric acid was diluted with purified water and added with potassium hydrogen phosphate and potassium dihydrogen phosphate to have concentration of 3.0% and 2.0%, respectively, to obtain 7.5% aqueous solution of inorganic phosphoric acid (liquid $B_3$) (pH: 1.73).

Example 4

(1) Production of Dispersion of Fluoro-Alumino-Silicate Glass Microparticles (Liquid $A_4$)

By using $SiO_2$: 29.1 g, $CaF_2$: 20.5 g, $Al_2O_3$: 13.3 g, CaO: 12.1 g, MgO: 10.2 g, $Na_2AlF_6$: 9.35 g, $KHCO_3$: 6.82 g, and $Ca_2(H_2PO_4)_2$: 2.38 g, glass was prepared by the same procedure as Example 2 and fluoro-alumino-silicate glass powder ($a_4$) having average particle diameter (D50) of 2.2 μm in volume-based particle size distribution was obtained. With the fluoro-alumino-silicate glass powder ($a_4$) having 18% concentration treated in the same manner as Example 1 using a bead mill, dispersion of the fluoro-alumino-silicate glass powder (liquid $A_4$) which has average particle diameter (D50) of 0.31 μm in volume-based particle size distribution and particle diameter of 1.11 μm at 90% position (D90) measured from the small diameter side in the volume-based particle size distribution was obtained. The glass dispersion (liquid $A_4$) has pH of 8.0.

(2) Preparation of Aqueous Inorganic Phosphoric Acid Solution (Liquid $B_4$)

Conc. phosphoric acid was diluted with purified water to obtain 10% aqueous solution of inorganic phosphoric acid (liquid $B_4$) (pH: 0.81).

Example 5

(1) Production of Dispersion of Fluoro-Alumino-Silicate Glass Microparticles (Liquid $A_5$)

By using $SiO_2$: 22.6 g, $ZrO_2$: 18.4 g, $Al_2O_3$: 17.3 g, $La_2O_3$: 15.7 g, $SrCO_3$: 13.8 g, $Na_2HPO_4$: 3.48 g, $CaO$: 3.24 g, $K_2HPO_4$: 3.16 g, $Al_2(HPO_4)_3$: 2.89 g, $CaF_2$: 2.37 g, and $Y_2O_3$: 1.58 g, glass was prepared by the same procedure as Example 1 and fluoro-alumino-silicate glass powder ($a_5$) having average particle diameter (D50) of 6.2 µm in volume-based particle size distribution was obtained. With the fluoro-alumino-silicate glass powder ($a_5$) having 10% concentration treated in the same manner as Example 1 using a bead mill, dispersion of the fluoro-alumino-silicate glass microparticles (liquid $A_5$) which has average particle diameter (D50) of 0.43 µm in volume-based particle size distribution and particle diameter of 1.94 µm at 90% position (D90) measured from the small diameter side in the volume-based particle size distribution was obtained. The glass dispersion (liquid $A_5$) has pH of 6.8.

(2) Preparation of Aqueous Inorganic Phosphoric Acid Solution (Liquid $B_5$)

Conc. phosphoric acid was diluted with purified water and added with potassium hydrogen phosphate and potassium dihydrogen phosphate to have concentration of 4.5% and 1.0%, respectively, to obtain 3.75% aqueous solution of inorganic phosphoric acid (liquid $B_5$) (pH: 2.87).

Example 6

Effect of Sealing Dentinal Tubules (1) Production of Pseudo-Hypersensitive Dentin Cow front tooth was extracted and the enamel layer was removed. To open dentinal tubules resembling hypersensitivity, the tooth was treated for 1 min in a 15% aqueous EDTA solution (pH 7.2). Herein below, it is referred to as a "pseudo-hypersensitive dentin."

(2) Experimental Method

The liquid A and liquid B described in each Example were admixed with each other at the recovery ratio described in Table 1 (change in pH of the mixture liquid was measured separately until two minutes after mixing), and applied on a pseudo-hypersensitive dentin using a microbrush for 20 seconds. After washing with water and drying, the treated surface was visually examined to determine any coloration of tooth surfaces. Subsequently, the surface treated with the sample and a cross section resulting from vertical cut using a micelle and mallet were observed under a field emission scanning electron microscope (JSM-7000F, manufactured by JEOL Ltd.). Then, based on a 500× enlarged observation image of the treated surface, sealing ratio of dentinal tubules (the number of sealed dentinal tubules in an image observed/the percentage of the number of dentinal tubules in an image observed) was calculated. At the same time, with energy dispersion X-ray spectroscopy (EDS), elemental analysis of the precipitates formed on the treated surfaces was carried out. A similar experiment was carried out for Comparative examples listed in Table 2. As Comparative example 1, a preparation in which the liquid A of the formulation liquid of Example 1 is prepared with a water dispersion of the fluoro-alumino-silicate glass microparticles, which have particle diameter of 3.34 µm (D50) and 6.63 µm (D90), was used. As Comparative example 2, Fluor•jelly (manufactured by BEE BRAND MEDICO DENTAL CO., LTD.) was used as an acidic fluoride coating agent (2% NaF:APF). As Comparative example 3, HYC (manufactured by SHOFU INC.) was used as a HY preparation, and as Comparative example 4, Saforide (manufactured by Oriental Pharmaceutical and Synthetic Chemical Co., Ltd.) was used as silver diamine fluoride. The treatments were performed according to a method designated for each preparation.

(3) Evaluation pH of the mixture liquid of each example right after mixing is given in Table 1. It was confirmed that pH is gradually increased after the mixing to reach pH of 4 to 6, which is appropriate for dental de-calcification and precipitation of Ca salts. In this case, the liquid A of Examples 1 to 5 exhibited full dispersion stability and no problems during its use. On the other hand, powder components of the liquid A of Comparative example 1 were precipitated during the use, exhibiting a problem in use. However, for the test, it was forcefully shaken and then used.

As a result of a naked eye observation of each treated surface, no clear change was observed from Examples 1 to 5 and the treatment with APF. However, according to the treatment with HY preparation of Comparative example 3, the treated surface was slightly dark. In Comparative example 4 in which silver diamine fluoride was used, strong black coloration was seen, indicating that both preparations have a problem in terms of aesthetics.

As a result of the observation of each treated surface under an electron microscope, Examples 1 to 5 and the treatment with the HY preparation or diamine fluoride all exhibited that the dentinal tubules were sealed with aggregates or precipitates derived from the preparation and the sealing ratio of the dentinal tubules was high. On the other hand, in Comparative example 1, the precipitates formed on tooth surfaces were large so that the sealing ratio of the dentinal tubules was low. In Comparative example 2 wherein the treatment with APF was carried out, the dentinal tubules remained open. Further, according to the observation under an electron microscope, the particle size of the precipitates that were precipitated by the treatment with the mixture liquid of Examples 1 to 5 was 0.01 to 1.0 µm, indicating that the particles size in the glass dispersion (liquid A) was faithfully reflected, and the treated surface was fully covered with the precipitates of the aforementioned size. According to observation of cross section, it was found that the dentinal tubule sealing material was precipitated with depth of about 10 µm and 15 µm by the treatments of Examples 1 to 5 and the silver diamine fluoride preparation, respectively. In case of the HY preparation, however, the surface was completely covered and no penetration into the dentinal tubules was observed.

With the energy dispersion X-ray spectroscopy (EDS), Si, Al and other glass-derived elements were identified based on elemental analysis of the precipitates on the surfaces treated with the treatments of Examples 1 to 5. It was also confirmed that they were the reaction products between the components of the glass dispersion (liquid A) and phosphoric acid.

TABLE 1

|  |  | Example 1 | Example 2 | Example 3 | Example 4 | Example 5 |
| --- | --- | --- | --- | --- | --- | --- |
| Liquid A | Composition of fluoro-alumino-silicate glass (addition composition before calcination) | $SiO_2$: 25.8 g<br>$Al_2O_3$: 20.9 g<br>$CaF_2$: 17.8 g<br>$La_2O_3$: 16.4 g<br>$Ca_2(H_2PO_4)_2$: 9.43 g<br>$Na_2CO_3$: 15.9 g<br>$CaO$: 0.50 g | $CaF_2$: 51.5 g<br>$CaO$: 16.3 g<br>$SiO_2$: 12.1 g<br>$Al_2(HPO_4)_3$: 8.26 g<br>$Al_2O_3$: 7.23 g<br>$Na_2AlF_6$: 4.52 g | $SiO_2$: 40.3 g<br>$Al_2O_3$: 33.8 g<br>$Na_2CO_3$: 15.5 g<br>$Al_2(HPO_4)_3$: 7.77 g<br>$Na_2AlF_6$: 5.31 g<br>$ZrO_2$: 2.82 g<br>$La_2O_3$: 0.24 g<br>$Y_2O_3$: 0.79 g | $SiO_2$: 29.1 g<br>$CaF_2$: 20.5 g<br>$Al_2O_3$: 13.3 g<br>$CaO$: 12.1 g<br>$MgO$: 10.2 g<br>$Na_2AlF_6$: 9.35 g<br>$KHCO_3$: 6.82 g<br>$Ca_2(H_2PO_4)_2$: 2.38 g | $SiO_2$: 22.6 g<br>$ZrO_2$: 18.4 g<br>$Al_2O_3$: 17.3 g<br>$La_2O_3$: 15.7 g<br>$SrCO_3$: 13.8 g<br>$Na_2HPO_4$: 3.48 g<br>$CaO$: 3.24 g<br>$K_2HPO_4$: 3.16 g<br>$Al_2(HPO_4)_3$: 2.89 g<br>$CaF_2$: 2.37 g<br>$Y_2O_3$: 1.58 g |
|  | Atomic ratio after calcination (converted based on oxide composition) * elements described in Claim "4" only | Si: 12.4 wt %<br>Al: 11.4 wt %<br>Na: 2.1 wt %<br>F: 8.9 wt % | Si: 5.1 wt %<br>Al: 5.2 wt %<br>Na: 1.0 wt %<br>F: 25.0 wt % | Si: 19.0 wt %<br>Al: 20.0 wt %<br>Na: 5.3 wt %<br>F: 3.3 wt % | Si: 13.0 wt %<br>Al: 8.0 wt %<br>Na: 2.2 wt %<br>K: 1.2 wt %<br>Mg: 5.9 wt %<br>F: 15.0 wt % | Si: 11.0 wt %<br>Al: 10.0 wt %<br>Na: 1.1 wt %<br>K: 1.4 wt %<br>F: 1.2 wt % |
|  | Volume-based particle size distribution (D50) | 0.38 μm | 0.42 μm | 0.33 μm | 0.31 μm | 0.43 μm |
|  | Volume-based particle size distribution (D90) | 0.77 μm | 1.27 μm | 1.44 μm | 1.11 μm | 1.94 μm |
|  | Glass dispersion concentration | 15% | 13% | 10% | 18% | 10% |
|  | pH | 8.6 | 10.2 | 7.3 | 8.0 | 6.8 |
| Liquid B | Composition | Phosphoric acid: 10%<br>Purified water: balance | Phosphoric acid: 15%<br>Purified water: balance | Phosphoric acid: 7.5%<br>$K_2HPO_4$: 3.0%<br>$KH_2PO_4$: 2.0%<br>Purified water: balance | Phosphoric acid: 10%<br>Purified water: balance | Phosphoric acid: 3.75%<br>$K_2HPO_4$: 4.5%<br>$KH_2PO_4$: 1.0%<br>Purified water: balance |
|  | pH | 0.81 | 0.67 | 1.73 | 0.81 | 2.87 |
| Liquid A:Liquid B (mixing ratio) |  | 1:1 (same amount) | 1:1 (same amount) | 2:3 | 3:2 | 1:1 (same amount) |
| Mixture liquid pH (right after being mixed) |  | 2.5 | 2.8 | 3.4 | 3.5 | 3.9 |
| Coloration on treated surface |  | No change | No change | No change | No change | No change |
| Dentinal tubule sealing ratio (observed under electron microscope) |  | 100% | 100% | 100% | 100% | 100% |

TABLE 2

|  |  | Comparative example 1 | Comparative example 2 | Comparative example 3 | Comparative example 4 |
| --- | --- | --- | --- | --- | --- |
| Liquid A | Composition of fluoro-alumino-silicate glass (addition composition before calcination) | $SiO_2$: 25.8 g<br>$Al_2O_3$: 20.9 g<br>$CaF_2$: 17.8 g<br>$La_2O_3$: 16.4 g<br>$Ca_2(H_2PO_4)_2$: 9.43 g<br>$Na_2CO_3$: 15.9 g<br>$CaO$: 0.50 g | Acidic fluoride coating agent (APF) | HY preparation | Silver diamine fluoride |
|  | Atomic ratio after calcination (converted based on oxide composition) * elements described in Claim "4" only | Si: 12.4 wt %<br>Al: 11.4 wt %<br>Na: 2.1 wt %<br>F: 8.9 wt % |  |  |  |
|  | Volume-based particle size distribution (D50) | 3.34 μm |  |  |  |
|  | Volume-based particle size distribution (D90) | 6.63 μm |  |  |  |
|  | Glass dispersion concentration | 15% |  |  |  |
|  | pH | 6.9 |  |  |  |
| Liquid B | Composition | Phosphoric acid: 10%<br>Purified water: balance |  |  |  |
|  | pH | 0.81 |  |  |  |
| Coloration on treated surface |  | No change | No change | Slight dark coloration | Strong dark coloration |
| Dentinal tubule sealing ratio (observed under electron microscope) |  | 20% | 0% | 100% | 100% |
| Remarks |  | Powder components in liquid A precipitated, and therefore it is not proper to use |  |  |  |

Example 7

Evaluation of Effectiveness on Dentinal Hypersensitivity During Orthodontic Treatment (1) Method Twenty patients suffering from gum recession caused by basic orthodontic treatment and hypersensitivity against air or cold caused by exposed dental roots were subjected for coating with the formulation liquid of Example 1 by which the liquid is applied to hypersensitive areas by rubbing for 20 seconds. After that, it was washed away with water and the measurement for evaluation was performed.

As a comparative example, Fluoden A (manufactured by Sunstar Inc.) as an acidic fluoride coating agent (2% NaF) was applied for 4 min but washing with water was not carried out.

(2) Measurement for Evaluation of Hypersensitivity Treatment

Evaluation to measure effectiveness of suppressing hypersensitivity was performed by observing the response of a subject (having subjective symptom) after an air is applied from an air syringe for 3 seconds, 1 cm apart from the tooth having a problem.

(3) Results

Most of the patients having dentinal hypersensitivity have experienced that, after receiving the treatment of Example 1 for 20 seconds, dentinal hypersensitivity disappeared and they feel no sensitive teeth (19 out of 20 people).

On the other hand, after 4-minute treatment of Comparative examples, no improvement in dentinal hypersensitivity was exhibited in 17 out of 20 people, who still had the hypersensitive teeth. Based on the results, it was confirmed that the composition of Example 1 of the instant invention has a significant effect of improving dentinal hypersensitivity.

Example 8

Acid Resistance Test (1) Method

It is known that the effect of the fluoride application on re-calcification of an enamel sample with caries in an early stage can be observed under in situ environment by using QUANTITATIVE Light-induced Fluorescence (QLF) method (Journal of Dental Health 57(1), 2-12, 2007).

The formulation liquid of Example 1 and Fluor•jelly (manufactured by BEE BRAND MEDICO DENTAL CO., LTD.) as an acidic fluoride coating agent (2% NaF) were applied to the enamel layer of a cow front tooth followed by de-calcification for 12 hours using a 0.1 M (0.92%) lactate buffer solution. Thereafter, the measurement according to QLF method (instrument for measurement: Quantitative Light-Fluorescence (trade name: QLF™, manufactured by Inspector Dental Care BV, herein under, also referred to as "QLF")) was carried out. As a result, $\Delta F$, which is a parameter indicating the correlation with the depth of de-calcification caused by dental caries at early stage, was calculated.

(2) Results $\Delta F$ value for the formulation of Example 1 was −0.8 while $\Delta F$ value for the acidic fluoride coating agent was −5.5. Thus, it was confirmed that significant acid resistance is obtained compared to the conventional technique (APF).

By applying the mixture liquid of the dispersion (A) and the aqueous solution (B) of the present invention to teeth, lots of fluorides can be efficiently introduced to the teeth with a short-time treatment so that high acid resistance can be given, re-calcification can be promoted, and secondary dental caries can be prevented. Further, according to the activity of microparticles of calcium fluoride, calcium phosphate and silicate cement that are generated during treatment for sealing dentinal tubules, a significant prophylactic effect against dentinal hypersensitivity can be obtained.

The present application is based on Japanese Application No. 2009-183093 which has been filed in Japan, and the entire content thereof is incorporated herein by reference.

The invention claimed is:

1. A preparation for oral cavity consisting of a mixture liquid obtained by mixing at the time of use a liquid (A), in which fluoro-alumino-silicate glass microparticles are dispersed in water at no less than 0.5% by mass to no more than 45% by mass concentration, wherein the fluoro-alumino-silicate glass microparticles have a particle diameter (D90) of 2 μm or less at 90% position when measurement is made from the small diameter side in a volume-based particle size distribution, and an aqueous inorganic phosphoric acid solution (B).

2. The preparation for oral cavity according to claim 1, wherein the liquid (A), in which fluoro-alumino-silicate glass microparticles are dispersed in water at no less than 0.5% by mass to no more than 45% by mass concentration, has pH of 6 to 12, the aqueous inorganic phosphoric acid solution (B) has pH of 0.5 to 4, and the mixture of (A) and (B) right after their mixing has pH of 2 to 4.

3. The preparation for oral cavity according to claim 1, wherein the fluoro-alumino-silicate glass microparticles comprise, as a constitutional elements, Si: 5 to 25% by mass, Al: 5 to 35% by mass, F: 1 to 25% by mass, and at least one selected from Na, K, and Mg: 1 to 10% by mass in total.

4. The preparation for oral cavity according to claim 1, wherein the preparation for oral cavity is a prophylactic agent for dental caries and/or a therapeutic agent for dental caries at early stage.

5. The preparation for oral cavity according to claim 1, wherein the preparation for oral cavity is a prophylactic and/or therapeutic agent for dentinal hypersensitivity.

6. The preparation for oral cavity according to claim 1, wherein the preparation for oral cavity is a material for the lining of a dentin cavity surface.

7. A kit for production of the preparation for oral cavity according to claim 1, the kit consisting of a combination of a liquid (A), in which fluoro-alumino-silicate glass microparticles are dispersed in water at no less than 0.5% by mass to no more than 45% by mass concentration, wherein the fluoro-alumino-silicate glass microparticles have a particle diameter (D90) of 2 μm or less at 90% position when measurement is made from the small diameter side in a volume-based particle size distribution, and an aqueous inorganic phosphoric acid solution (B).

* * * * *

UNITED STATES PATENT AND TRADEMARK OFFICE
CERTIFICATE OF CORRECTION

PATENT NO. : 8,354,117 B2
APPLICATION NO. : 13/387992
DATED : January 15, 2013
INVENTOR(S) : Masayoshi Tsunekawa et al.

It is certified that error appears in the above-identified patent and that said Letters Patent is hereby corrected as shown below:

In the Claims:

In Column 18, claim 1, line 21;
Delete

"concentration"

In Column 18, claim 2, line 30;
Delete

"concentration"

In Column 18, claim 7, line 54;
Delete

"concentration"

Signed and Sealed this
Fourteenth Day of May, 2013

Teresa Stanek Rea
*Acting Director of the United States Patent and Trademark Office*